(12) United States Patent
Yang et al.

(10) Patent No.: US 8,597,938 B2
(45) Date of Patent: Dec. 3, 2013

(54) SYSTEM FOR PROVIDING CONTROL REACTIONS FOR REAL TIME RT-PCR

(75) Inventors: Jingping Yang, Gaithersburg, MD (US); Li Shen, Boyds, MD (US)

(73) Assignee: QIAGEN Sciences LLC, Germantown, MD (US)

( * ) Notice: Subject to any disclaimer, the term of this patent is extended or adjusted under 35 U.S.C. 154(b) by 270 days.

(21) Appl. No.: 12/249,791

(22) Filed: Oct. 10, 2008

(65) Prior Publication Data

US 2009/0124516 A1  May 14, 2009

Related U.S. Application Data

(60) Provisional application No. 60/979,705, filed on Oct. 12, 2007.

(51) Int. Cl.
*C12M 1/34* (2006.01)
*C12P 21/02* (2006.01)

(52) U.S. Cl.
USPC ............... 435/288.3; 435/288.2; 435/287.2; 435/286.3; 435/283.1; 506/16; 506/13

(58) Field of Classification Search
USPC ............ 506/13, 16; 435/288.3, 288.2, 287.2, 435/286.3, 283.1
See application file for complete search history.

(56) References Cited

U.S. PATENT DOCUMENTS

| | | | |
|---|---|---|---|
| 6,103,192 A * | 8/2000 | Stapleton et al. | 422/50 |
| 6,852,494 B2 * | 2/2005 | Liao et al. | 435/6 |
| 2005/0260640 A1 * | 11/2005 | Andersen et al. | 435/6 |
| 2007/0161031 A1 * | 7/2007 | Trinklein et al. | 435/6 |
| 2008/0293045 A1 * | 11/2008 | Piepenburg et al. | 435/6 |
| 2010/0233699 A1 * | 9/2010 | Nazarenko et al. | 435/6 |

OTHER PUBLICATIONS

Applied Biosystems (2009) "SYBR Green PCR Master Mix and RT-PCR Reagents," *Protocol* Part No. 4310251 Rev. E.
Arikawa, E. (Apr. 21, 2008) "Seeing is Believing? Development of a Rigorous Control Panel for qRT-PCR," Presentation given at the Cambridge Healthtech Institute's Quantitative PCR Meeting, San Diego, CO. Abbreviated Version Prepared by Ray Blanchard of SABiosciences.
Bustin et al. (Sep. 2004) "Pitfalls of Quantitative Real-Time Reverse-Transcription Polymerase Chain Reaction," *J. Biomol. Techniques* 15(3):155-166.
Bustin, S.A. ed. (2004) *A-Z of Quantitative PCR*, International University Line, La Jolla, California, pp. 448-459.
Livak et al. (2001) "Analysis of Relative Gene Expression Data Using Real-Time Quantitiative PCR and the $2^{-\Delta\Delta CT}$ Method," *Methods* 25:402-048.
Nolan et al. (Web Release Nov. 9, 2006) "Quantification of MRNA Using Real-Time RT-PCR," *Nature Protocols* 1(3):1559-1582.
Nolan et al. (Web Release Feb. 20, 2006) "SPUD: A Quantitative PCR Assay for the Detection of Inhibitors in Nucleic Acid Preparations," *Anal. Biochem*.351:308-310.
Pinto et al. (Jul. 5, 2006) "Generation of Non-Genomic Oligonucleotide Tag Sequences for RNA Template-Specific PCR," *BMC Biotechnol.* 6:31, 7 pages.
SABiosciences (Jun. 6, 2008) "$RT^2$ Profiler PCR Array System," User Manual, Part #1022A, Version 3.3, SABiosciences Corporation, 6951 Executive Way, Fredrick MD 21703, USA.
Zhang et al. (2003) "Millions of Years of Evolution Preserved: A Comprehensive Catalog of the Processed Pseudogenes in the Human Genome," *Genome Res*.13:2541-2558.

* cited by examiner

*Primary Examiner* — Teresa Wessendorf
(74) *Attorney, Agent, or Firm* — Seed IP Law Group PLLC

(57) ABSTRACT

Provided are methods and oligonucleotides useful as primers and templates for internal controls designed for use in Real Time Reverse Transcriptase Polymerase Chain Reactions. Use of the present methods and oligonucleotides allows validation of assay parameters and of the results that an assay set.

11 Claims, 3 Drawing Sheets

US 8,597,938 B2

SYSTEM FOR PROVIDING CONTROL REACTIONS FOR REAL TIME RT-PCR

CROSS REFERENCE TO RELATED APPLICATIONS

This application claims benefit of U.S. Provisional Application No. 60/979,705, filed Oct. 12, 2007, which is incorporated by reference herein.

ACKNOWLEDGEMENT OF FEDERAL RESEARCH FUNDING

Not applicable.

BACKGROUND OF THE INVENTION

The present invention relates to the inclusion of control reactions in real time reverse-transcriptase-initiated polymerase chains reactions, as applied to certain experiments in molecular biology.

The Polymerase Chain Reaction (PCR) is widely used to detect DNA sequences by amplifying their number by an exponential cyclic biochemical process. Purified RNA may be transcribed using enzymes known as reverse transcriptases to generate a DNA sequence that is complementary to all or part of the RNA. Such DNA made by reverse transcription, especially when the RNA that is reverse transcribed is mRNA, is known as complementary DNA (cDNA), which may then be amplified using PCR. This combined process is known as RT-PCR. As PCR proceeds, the number of copies of the amplified DNA increases and a number of methods and instruments that automate amplification and measurement of the products of amplification have been developed and are widely used. By continually monitoring in "real time" the progress of amplification reaction from its start, the number of DNA molecules present at the start of the process can be determined. This method is generally know as Quantitative Real-Time PCR and is an exceptionally sensitive method for detecting and quantitating small numbers of DNA molecules of a particular sequence. If reverse transcription is carried out on a sample of RNA to generate cDNA and the cDNA so generated is then amplified by Quantitative Real Time PCR, then the number of RNA molecules of a particular sequence may be determined. This process is commonly referred to as Quantitative Real-Time RT-PCR.

For this method to be most quantitative and reliable, the inclusion of artificial control reactions among the experimental reactions is desired. These controls primarily address potential causes of spurious or inaccurate results. First, impurities may be carried through purification or otherwise enter the samples being assayed which may inhibit the PCR process. Second, impurities may be carried through the purification of RNA or otherwise enter the samples which inhibit the reverse transcription reaction. Third, genomic DNA may have been carried through the purification process, which is designed to eliminate it, and may be amplified at the final PCR step producing amplified product that may falsely indicate the existence of more mRNA of a particular sequence than is actually present in the sample. In any set of Quantitative Real Time RT-PCR assays, redundant controls addressing all three of the above concerns may be desired. Having these controls configured conveniently along side experimental assays in a format compatible with automated processing and data collection is further desired. In addition, it may be desirable to include in a set of assays control reactions that detect mRNAs that would be expected to be present at roughly predictable levels. These mRNAs commonly code for proteins that are involved in basic cellular metabolism or are components of ubiquitous and necessary cellular structures such as ribosomes or the cytoskeleton. Genes coding for such proteins are often referred to as housekeeping genes.

Quantitative Real-Time RT-PCR is widely used to monitor the levels of multiple mRNAs in tissues or other collections of cells. Often the various mRNAs being monitored in a single experiment are related. In such an experiment one wishes to monitor the relative levels the various mRNAs but must meet the underlying assumption that all samples being compared are of similar quality. The process of preparation of mRNA from cells, reverse transcription and amplification, however careful a practitioner may be, may be less than optimal or may proceed with variable efficiency. To control for this possibility, it is advisable to include one or more control reactions to monitor reaction efficiency and quality of sample preparation. Moreover, detection of these mRNAs at unexpectedly low levels may alert the experimenter to suboptimal quality of the assayed samples or their preparation. Certain mRNAs are expressed in substantially all cells of a species, sperm being a notable exception to this generalization, at high to moderate levels and detection of one or several of these mRNAs may be used to monitor purification yield and serve as reference levels for expression of mRNAs that one wishes to measure in one's assay. Genes and their mRNA transcripts that code for protein involved in fundamental cellular metabolism or are components of cellular structures are examples and are commonly referred to as housekeeping genes.

SUMMARY OF THE INVENTION

The invention comprises multiple control reaction mixtures comprising primers or primers and template nucleic acid for use in increasing the reliability and validity of quantitative real-time RT-PCR assays, particularly such assays done in microtiter plates. These control reaction mixtures help experimenters monitor the quality of samples and sample preparation used in performing these assays. More particularly these control reaction mixtures help monitor contamination by inhibitors of reverse transcription or PCR amplification, as well as undesired contamination by genomic DNA and suboptimal purification of mRNA. The use of combined control assay panels enables accurate and consistent relative measurements of gene expression from multiple samples across multiple PCR runs. In an embodiment there is a an array of wells in a microtiter plate, wherein the wells independently of one another contain primers comprising RT-PCR primers for amplifying genomic DNA of an organism of interest, for amplifying at least one nucleic acid molecule characterized by a nucleotide sequence which is not known to occur in nature, together with that nucleic acid molecule (see, for example, FIG. 2).

DETAILED DESCRIPTION OF THE INVENTION

Figure 1:
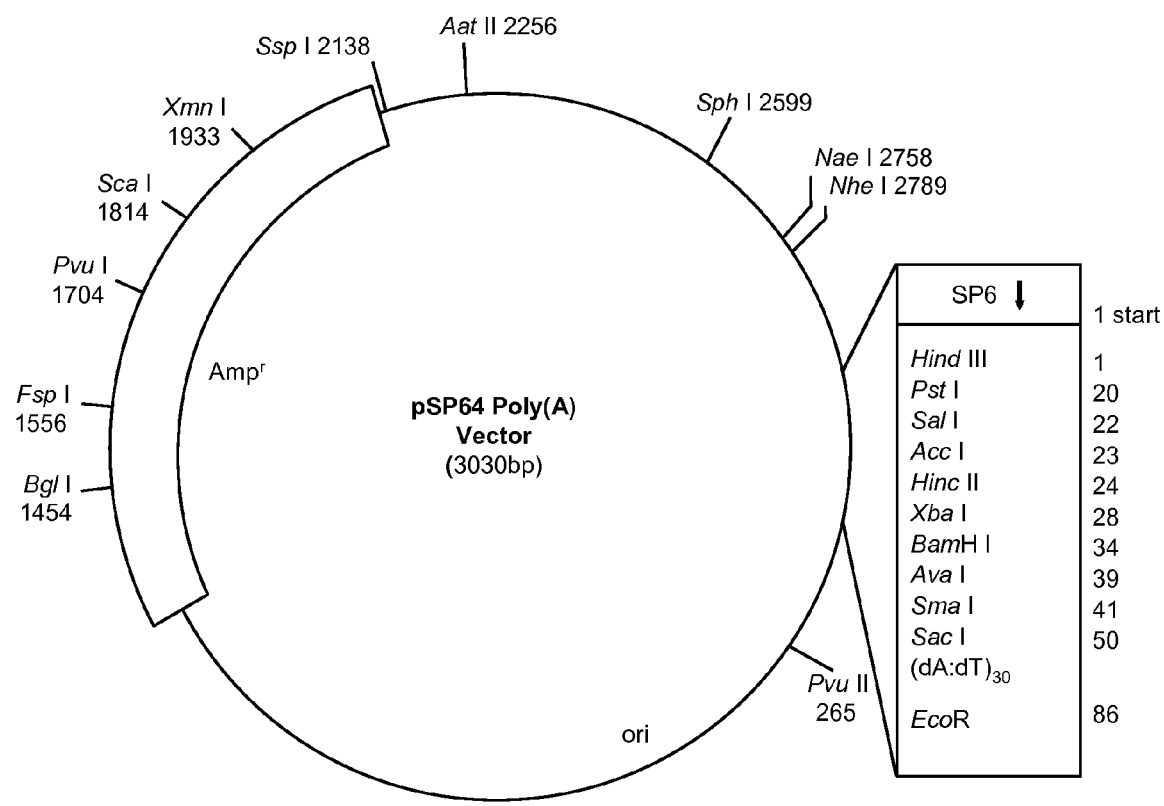
FIG. 1 depicts a commercially available plasmid vector (Promega Corporation, Madison, Wis.) into which any control DNA template may be cloned for propagation, and if desired in vitro transcription, in the plasmid shown carried out using SP6 RNA polymerase, may be used to synthesize RNA for use as a control.

Instruments designed to carry out Quantitative Real-Time PCR commonly utilize microtiter plates that conform to SBS Standards and have 96 or 384 wells.

Use of such plates for arrays of individual assays facilitates the analysis of multiple related mRNAs across multiple samples and the use of automated instruments. The following description specifically relates to a 96 well SBS format microtiter plate but is applicable to microtiter plates containing multiples of 96 wells, or multiwell formats other than the SBS format. Adaptation to these formats can be straightforward. Most of the wells of a typical 96 well plate are loaded with different pairs of primers specific for amplification of various sequences that may be present in varying quantities in samples prepared by the user of the array. Commonly these several primer pairs will be specific for the amplification of sequences found in mRNAs that code for enzymes or other proteins involved in a metabolic or cellular control pathway or process.

The term SBS standard refers to the standard for footprint, height, bottom outside flange, and well positions published in 2004 by the American National Standards Institute as publications ANSI/SBS 1-2004, ANSI/SBS 2-2004, ANSI/SBS 3-2004 and ANSI/SBS 4-2004, which are hereby incorporated by reference.

Into several adjacent wells, most preferably in the last row, of a microtiter plate are loaded with the following control reagents with each control well containing only reagents for one of the following control reactions. Each microtiter plate will most desirably contain a full complement of controls.

Provided herein is a control RNA (RTC) comprising a sequence that consists of a random sequence that does not share substantial homology with any known natural sequence, and which owing to its length, is believed unlikely to share substantial homology with any yet to be discovered sequence in nature. Alternatively, a sequence from a class of organisms distantly related or unrelated to the organism that one would be obtaining cells for testing can be used. For example, a sequence from a plant can be used as a control in an array designed for assaying human sequences. The uniqueness of an artificial sequence or the phylogenetic distance in the case of a naturally occurring sequence means that the probability of it being amplifiable with a set of PCR primers designed to amplify a sequence being assayed in the array will be exceptionally low. Inclusion of this RNA, by addition of a fixed amount to the sample prior to cDNA synthesis, allows the experimenter to detect the presence of any non-specific inhibitor of reverse transcription that may contaminate the sample following preparation as such a contaminating inhibitor will reduce the yield of the control RNA below its expected value. Together with this RNA, PCR primers (RTC Assay) that will amplify this sequence uniquely are also included in wells prepared for this control reaction. Inhibition of this control is indicative of such an inhibitor contaminating the prepared sample and would thereby call into question the validity of results from other RT-PCR assays intended to measure specific mRNA levels in the experimental sample.

An external RNA control of a known number of copies is added into the first strand cDNA synthesis reaction. RNA is generated by in vitro transcription and added to RT primer mix. The in vitro polyadenylated transcript with an artificial sequence wherein there is no known homology to any human, mouse or rat sequences. This can be used in conjunction with the Reverse Transcription Control (RTC) and Plate positive control (PPC) assays to monitor the presence of reverse transcriptase inhibitors and the efficiency of reverse transcription process.

Below are shown sequences than are suitable for inclusion as such a control RNA (RTC) for the above purpose:

Primer regions (GGGTGGAGGTCCCTATGGTC, SEQ ID NO:1; and complement of AGCTGATCTCCGAGGTG-CAG, nucleotides 415-434 of SEQ ID NO:3, i.e. CTGCAC-CTCGGAGATCAGCT, SEQ ID NO:2) are shown in bold italics and primers may be made complementary to either strand to effect amplification with two primers which are complementary to sequences on opposite strands. This sequence (SEQ ID NO:3) and all others listed herein are listed in the conventional 5' to 3' orientation.

CTCGTTGTTCTCCTGCTGCAACATCTCTCAGAAACCATCTCTCTTTTCTC

CGTCTTCTCGTAGTTCTCATTGTCCCATTCGTTGCTCACAGTCACAGGAA

GGGAAAGAAGTGGTTACCAGTCCTTTGAGAAGTGTGGTTTGGTCATTAGG

AGAAGAGGTTTCAAAGAGAAGTCTATTTGCACTTGTCTCTGCTTCTCTCT

TCTTTGTTGATCCTGCTCTTGCTTTTAAG*GGTGGAGGTCCCTATGGTC*

AAGGAGTCACCAGGGGACAGGACCTATCTGGCAAAGATTTCAGTGGCCAG

ACTCTTATCAGGCAGGACTTCAAAACGTCCATCCTAAGGCAAGCCAACTT

CAAGGGTGCAAAGTTGTTAGGTGCTAGCTTCTTTGATGCAGATCTAACAG

GTGCTGATTTATCGGA*AGCTGATCTCCGAGGTGCAG*ATTTCTCCTTGG

CAAATGTAACAAAGGTGAATCTAACGAACGCTAACTTAGAAGGAGCGACT

GTTACTGGAAACACATCATTCAAGGGATCAAACATTGCAGGCGCAGACTT

CACTGATGTCCCGGGCGAGCTCCCAAAAAAAAAAAAAAACCGAATTC

A control DNA (PPC) comprising a sequence that consists of a random sequence that does not share substantial homology with any sequence yet discovered in nature, and which owing to its length, is unlikely to share substantial homology with any yet to be discovered sequence in nature is provided. Alternatively, a sequence from a class of organisms distantly related or not related to the organism that one would be obtaining cells for testing can be used. For example, a sequence from a plant can be used as a control in an array designed for assaying human sequences. The uniqueness of an artificial sequence or the phylogenetic distance in the case of a naturally occurring sequence means that the probability of it being amplifiable with set of PCR primers designed to amplify a sequence being assayed in the array will be exceptionally low. Sequences from an animal could be used as control as control in arrays designed to measure expression of cells from plants. Sequences from bacteria, including bacteria found only in exotic environments could also be used for this purpose. Inclusion of this DNA in a PCR reaction well with primers to amplify it allows the experimenter to detect the presence of any non-specific inhibitor of PCR that may contaminate the sample following preparation as such a contaminating inhibitor will reduce the yield of the control DNA below its expected value. The sequence of this DNA used as a control in an array is preferably different from that on the aforementioned control RNA used in the same array and is amplified by primers other than those used to amplify cDNA generated by reverse transcription of the control RNA. Primers (PPC Assay) to amplify this control DNA are included in the wells prepared for this control reaction.

An external DNA template of a known number of copies and a primer pair to detect it are included in a separate assay. The template is closely related to the RTC RNA; it shares significant amount of identity except at region of downstream PCR primers, which will not amplify cDNA from RTC and RTC primers will not amplify PPC DNA, but amplicon efficiencies and sensitivities are almost the same. This aspect of the reaction produces a defined $C_t$ value under proper PCR conditions.

The PPC is an artificial sequence with no known homology to any human, mouse or rat sequences.

As used herein Ct stands for Cycle threshold; it is the quantitative unit of measure used as output for real-time PCR.

Below are shown sequences that are suitable for inclusion as such a control DNA for the above purposes: Suitable primer sequences or their complements are shown in italics within each of the sequences below. Other primer sequences may be used, but the ones (AGCTGATCTCCGAGGTGC, SEQ ID NO:4 and sequence complementary to ACAGCAAACACGGTACGAGAG, i.e., nucleotides 589-607 of SEQ ID NO:6, i.e., CTCTCGTACCGTGTTTGCTGT, SEQ ID NO:5) shown within the sequence below (SEQ ID NO:6) are sufficiently specific for the purposes of this invention.

CCTGCTGCAACATCTCTCAGAAACCATCTCTCTTTTCTCCGTCTTCTC

GTAGTTCTCATTGTCCCATTCGTTGCTCACAGTCACAGGAAGGGAAAG

AAGTGGTTACCAGTCCTTTGAGAAGTGTGGTTTGGTCATTAGGAGAAG

AGGTTTCAAAGAGAAGTCTATTTGCACTTGTCTCTGCTTCTCTCTTCT

TTGTTGATCCTGCTCTTGCTTTTAAGGGTGGAGGTCCCTATGGTCAAG

GAGTCACCAGGGGACAGGACCTATCTGGCAAAGATTTCAGTGGCCAGA

CTCTTATCAGGCAGGACTTCAAAACGTCCATCCTAAGGCAAGCCAACT

TCAAGGGTGCAAAGTTGTTAGGTGCTAGCTTCTTTGATGCAGATCTAA

CAGGTGCTGATTTATCGGA*AGCTGATCTCCGAGGTGC*AGATTTCTCCT

TGGCAAATGTAACAAAGGTGAATCTAACGAACGCTAACTTAGAAGGAG

CGACTGTTACTGGAAACACATCATTCAAGGGATCAAACATTGCAGGCG

CAGACTTCACTGATGTCCCCTGGTCGATGGTACGGATGGTTGTATAGA

TATACACAATCA*ACAGCAAACACGGTACGAGAG*CTCCAAAAAAAAAA

AAAAACCGAATTC

A pair of primers (GDC, genomic DNA contamination control) that specifically amplify only a sequence of DNA that is highly conserved in all humans in multiple copies, e.g. a satellite sequence or as a single copy per diploid genome, but which is substantially not transcribed into RNA are provided. In the present context, substantially not transcribed means that the level of transcription, if there is transcription, is below the detection limit of the assay. Genomic DNA that may contaminate the preparation of mRNA from which cDNA is synthesized by reverse transcription can yield a falsely elevated result regarding the levels of any particular mRNA present in the sample. Use of a sequence found in multiple copies may provide a more sensitive assay for detection of genomic DNA but this level of sensitivity may not be preferred in practice and a single copy may be preferred. This DNA may be provided as a segment within a plasmid that can be prepared from a bacterium or may be an amplification product prepared by in vitro synthesis or may be provided in any of a number of forms well known in the art of molecular biology and nucleic acid biochemistry or chemistry. Genomic DNA may act as an effective template during PCR and result in undesirable false positive signals unrelated to mRNA level in the sample. Cross-intron RT-PCR assay designs cannot always prevent amplification from the contaminating genomic DNA due to the presence of 1 or more processed pseudogenes for many genes in the genome.

Removal of genomic DNA from RNA samples by methods such as DNAse treatment is recommended, especially when measuring transcripts expressed at low levels. However, effectiveness of such treatment is variable, leading to a requirement to assess this outcome Primer pairs suitable for inclusion in reaction mixture design to detect contaminating human, mouse and rat genomic DNA follow:

For arrays designed for use with sample purified from human cells either of the following two primer pairs is preferred; (all written in the conventional 5' to 3' orientation):

```
Pair #1:
GATTGCATTCAAGTCACACA      (SEQ ID NO:7)
and

GCTCGAACACAAACATCAC       (SEQ ID NO:8)

Pair #2:
CACCCATGATATGCCTTAGC      (SEQ ID NO:9)
and

TTCTGCTGAACCCAAGAGC       (SEQ ID NO:10)
```

For arrays designed for use with sample purified from mouse cells any of the following two primer pairs are preferred; (written in the conventional 5' to 3' orientation)

```
Pair #1:
TTAGGACGTGAAGTTTGGTG      (SEQ ID NO:11)
and

CCTTCAGTGTGCATTTCTC       (SEQ ID NO:12)

Pair #2:
ATCCCATGATGTTGCCAAG       (SEQ ID NO:13)
and

TGTCTGGCTCGGTGTTTAC       (SEQ ID NO:14)
```

For arrays designed for use with sample purified from rat cells the following primer pair is preferred; (written in the conventional 5' to 3' orientation)

```
TCTGCCTCTCAATACCATCATC    (SEQ ID NO:15)
and

TGAACAAAGAGAAACTGTCCAG    (SEQ ID NO:16)
```

In addition to the above controls, several wells of the microtiter plate may contain PCR primer pairs that are specific for mRNAs that are present in essentially all human cells and which code for proteins or enzymes that provide what are commonly referred to as housekeeping functions (HKG). These primer pairs provide confirmation that preparation of the mRNA achieved a required yield and that integrity of the mRNA was maintained during preparation. Most preferably these control wells are placed in the same row as the aforementioned controls. Primer pairs suitable for amplifying mRNAs coding for the above housekeeping genes include the following primer pairs that amplify the following human, mouse, and rat mRNAs designated by the name of the protein they encode and in parentheses their corresponding gene symbols shown. All primer sequences are listed in the 5' to 3' orientation.

```
Human:
Beta-2-microglobulin (B2M)
GCAAGGACTGGTCTTTCTATCTC      (SEQ ID NO:17)
and

ACTTAACTATCTTGGGCTGTGAC      (SEQ ID NO:18)

Hypoxanthine guanine phosphoribosyl
transferase 1 (HPRT1)
GGCCATCTGCTTAGTAGAGC         (SEQ ID NO:19)
and

TTAGGAATGCAGCAACTGAC         (SEQ ID NO:20)

Ribosomal protein L 13a (RPL 13A)
TGAGTGAAAGGGAGCCAGAAG        (SEQ ID NO:21)
and

TGCAGAGTATATGACCAGGTG        (SEQ ID NO:22)

Glyceraldehyde-3-phosphate dehydrogenase
(GAPDH)
AGAGCACAAGAGGAAGAGAGAG       (SEQ ID NO:23)
and

GGTTGAGCACAGGGTACTTTATTG     (SEQ ID NO:24)

Actin, beta (ACTB)
AATGCTTCTAGGCGGACTATG        (SEQ ID NO:25)
and

CTCCAACCGACTGCTGTCAC         (SEQ ID NO:26)

Mouse:
Glucuronidase, beta (Gusb)
GTAATATGTCCTGCTGAGAGGTG      (SEQ ID NO:27)
and

CTTAAATTGTGAGCCAGCCTTC       (SEQ ID NO:28)

Hypoxanthine guanine phosphoribosyl
transferase (Hprt1)
GGCCATCTGCCTAGTAAAGC         (SEQ ID NO:29)
and

GGACGCAGCAACTGACATTTC        (SEQ ID NO:30)

Heat shock protein 90 kDA alpha (cytosolic)
class B member 1 (Hsp90ab1)
GGCTCTCTGCTCATGTCTACAAG      (SEQ ID NO:31)
and

AACCACAATACATAACACCCAAC      (SEQ ID NO:32)

Glyceraldehyde-3-phosphate dehydrogenase
(Gapdh)
TATGACTCCACTCACGGCAAATTC     (SEQ ID NO:33)
and

ACATACTCAGCACCGGCCTC         (SEQ ID NO:34)

Actin, beta, cytoplasmic (Actb)
GGCTGTATTCCCCTCCATCG         (SEQ ID NO:35)
and

CCAGTTGGTAACAATGCCATGT       (SEQ ID NO:36)

Rat:
Ribosomal protein, large P1 (Rplp1)
CTAAGGCCGCGTTGAGGTG          (SEQ ID NO:37)

and

CAGGCAAGCTCAGAGACAGAAG       (SEQ ID NO:38)

Hypoxanthine guanine phosphoribosyl
transferase (Hprt)
TTAGAAATGTCTGTTGCTGCGTC      (SEQ ID NO:39)
and

GATCTGTCTGTCTCACAAGGGAAG     (SEQ ID NO:40)

Ribosomal protein L 13a (Rpl13A)
AGTATCTGGCCTTTCTCCGAA        (SEQ ID NO:41)
and

GATCCCATCCAACACCTTGAG        (SEQ ID NO:42)

Lactate dehydrogenase A (Ldha)
AGCTGAAAGGTTACACATCCTG       (SEQ ID NO:43)
and

TTCATTATGCTCTCGGCCAAG        (SEQ ID NO:44)

Actin, beta (Actb)
TGTGTGGATTGGTGGCTCTATC       (SEQ ID NO:45)
and

CTCAGTAACAGTCCGCCTAGAAG      (SEQ ID NO:46)
```

Figure 2:
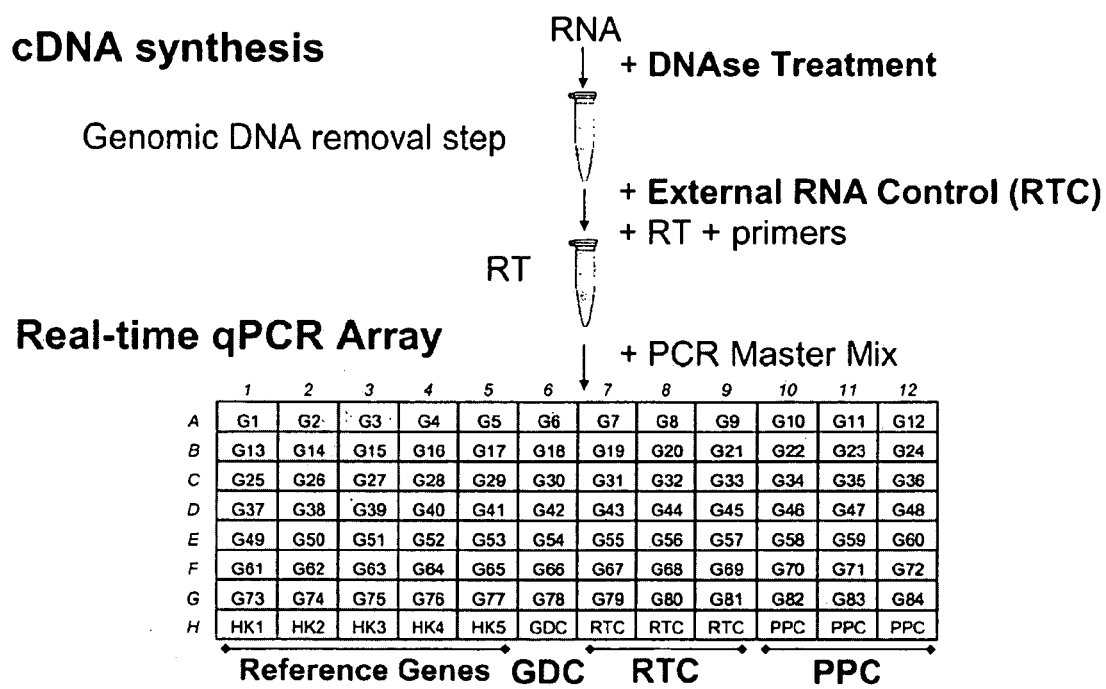
FIG. 2 shows that steps in carrying out the RT-PCR assay and an exemplary array employing the strategy and primers of the present invention.
Figure 3:
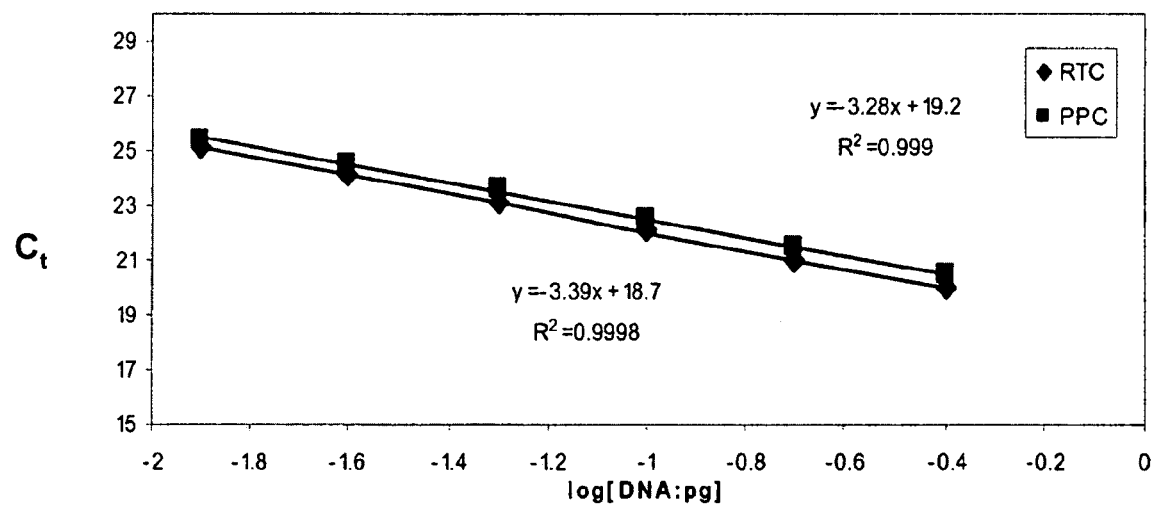
FIG. 3 illustrates similar amplification efficiencies for RTC and PPC assays run as described herein. Quality control criteria are as follows: For PPC, the expected $C_t$ value is 20± and a PPC $C_t$>22 indicates inhibition of the PCR. For RTC, the expected (RCT $C_t$–PPC $C_t$)=2.5, and values greater than 5 indicate the inhibition of cDNA synthesis.

The 12 wells available in a row on a microtiter plate from 1 to 3 may be allocated to controls for inhibition of reverse transcription. From 1 to 3 of these wells may be allocated to controls for inhibition of PCR, 1 to 3 of these wells may be allocated to controls for contamination by genomic DNA, and 3 to 9 of these wells may be allocated to controls for yield of mRNAs coding for housekeeping proteins. The foregoing numbers of wells for each set of controls is illustrative and suggestive of a reasonable use of wells for controls; however, use of other numbers of wells, both in absolute number and relative to the number of wells used for the different controls is also possible and is within the scope of this invention. FIG. 2 provides an exemplary control panel array for carrying out controlled reactions as described herein. Reaction mixtures comprising the appropriate nucleic acid molecules (primer pair and as needed a control template nucleic acid molecule). Moreover, the wells allocated for use as controls may be located anywhere within the array. Among the genes which work well as controls in this context are H1-5: HKG, H6: GDC, H7-9: RTC and H10-12: PPC. Use of all of these or possibly other ones as well can provide redundancy with respect to quantitative reference of expression of other mRNAs. Similar genes from other species than human, mouse, or rat can be used in arrays designed for assay of mRNAs from cells of these species.

The above controls, in addition to detecting severely deficient performance in the preparation of a sample, also permit one to calibrate the quantitative results to the output of the controls thereby increasing the precision and reliability of the experimental results obtained. By including a full and redundant set of control samples in each microtiter plate, the accuracy of calibration is further enhanced since variation between microtiter plates can be accounted for.

An RNA prepared from a single biological sample may be the only experimental sample assayed in a single microtiter plate. The controls on each plate can inform the experimenter of the presence or level of inhibitors of reverse transcription or PCR, or of contamination by genomic DNA for each individual sample. Additionally, as each microtiter plate can be prepared using the same control materials, primers and/or template variation in the amplification among different plates can inform an experimenter of variability in the efficiency of RNA preparation among different samples and of the variation in purity with respect to inhibitors of reverse transcription or PCR among the samples.

Shown below (FIG. 1) is a commercially available plasmid vector (Promega Corporation, Madison, Wis.) into which any control DNA template may be cloned for propagation, and if desired in vitro transcription, in the plasmid shown carried out using SP6 RNA polymerase, may be used to synthesize RNA for use as a control. A DNA sequence corresponding to a control DNA or RNA is conveniently cloned into the multiple cloning site using any number of restriction endonucleases and methods well known in the art. Other plasmid vectors as well as viral vectors are known that are widely available and well known and which contain similar sequences, e.g. promoters useful for in vitro transcription that can be used in place of the plasmid vector shown below.

Table 1 shows real-time PCR results demonstrating the specificity and sensitivity of the human genomic DNA assay #2. Incremental amounts of human genomic DNA (gDNA) ranging from none to 61 haploid copies of the genome were measured in a background of cDNA obtained from reverse transcription of 0 (NTC), 0.5, 1.0 and 10 ng human universal RNA (Biochain Inc., Hayward, Calif.). The results show no detectable response in the absence of any gDNA and a consistent incremental increase in $C_t$ values corresponding to the increased copy number. It is noteworthy that as little as a single DNA copy can be detected in these assays. In addition, the GDC control can function as an effective surrogate for RT-minus assays, and it can be used in place of RT-minus assays to monitor genomic DNA contamination for any gene of interest in RT-PCR assays. See Tables 2 and 3. Genomic DNA contamination affects $C_t$ values for target genes expressed at relatively low levels.

TABLE 1

Real-Time PCR results demonstrating the specificity and sensitivity of the human genomic DNA assay #2

| gDNA pg (copy number) | NTC | RT from 0.5 ng RNA | RT from 1 ng RNA | RT from 10 ng RNA |
|---|---|---|---|---|
| 0 | ND | ND | ND | ND |
| 3.3 (1) | 33.4 | 33.8 | 32.5 | 33.6 |
| 6.6 (2) | 32.1 | 33.5 | 32.1 | 32.7 |
| 13.2 (4) | 31.1 | 30.8 | 31.3 | 31.9 |
| 26.4 (8) | 30.3 | 30.0 | 30.9 | 30.5 |
| 52.8 (16) | 29.2 | 29.0 | 29.3 | 30.1 |
| 100 (30) | 28.3 | 28.2 | 28.3 | 29.2 |
| 200 (61) | 27.4 | 27.3 | 27.3 | 27.7 |

TABLE 2

Comparison between RT-minus Assays and GDC Control Assay

| Average Ct | Untreated RNA RT-minus | DNAse treated RNA RT-minus | RT |
|---|---|---|---|
| 89 RT-PCR Assays | 28.8 to 38.6 | 36.3 to 40 | 17.9 to 36.1 |
| GDC | 30.1 | 34.5 | 35.1 |

TABLE 3

GDC Control Can Substitute for RT-minus assays.

| RNA Sample Treatment | Ct for FOXP3 RT-PCR | Ct for FOXP3 RT-minus | Ct for GAPDH RT-PCR | Ct for GAPDH RT-minus | Ct for GDC RT-PCR | Ct for GDC RT-minus |
|---|---|---|---|---|---|---|
| Untreated | 29.2 | 30.6 | 15.4 | 25.9 | 26.6 | 27.1 |
| DNAse Treated | 33.0 | ND | 15.8 | ND | ND | ND |

EXAMPLE

Total RNA from human, mouse or rat cells was isolated by a standard mini-column method, RNAeasy® Mini Kit (Qiagen, Valencia, Calif.). RNA sample quality was evaluated by examining electrophoretic integrity of 18S and 28S rRNA bands on a 2100 Bioanalyzer instrument (Agilent, Santa Clara, Calif.) and by standard spectrophotometric absorbance methods at 230, 260 and 280 nm wavelengths. Preparation of cDNA from the RNA samples was carried out using a standard 20 µl reverse transcriptase (RT) reaction from the QUANTI TECT™ Reverse Transcription Kit (Qiagen). Some samples were not treated with the DNase (gDNA Wipeout Buffer, Qiagen) step to preserve the levels of genomic DNA contamination left behind after the mini-column purification. One modification to the RT reaction was the addition of a fixed amount of RTC RNA control template to the kit's RT Primer Mix prior to initiating the enzymatic reaction so that the RTC RNA would be converted to cDNA along with the sample RNA. Upon completion of the reverse transcription protocol, the cDNA sample was diluted with 91 µl nuclease-free water (~5 fold) so that 1 µl (~1/100) was used as the template for each individual 25 µl PCR reaction on the PCR arrays.

SYBR® Green (Molecular Probes, Eugene, Oreg.) real-time PCR was set up by combining 1275 µl 2×SYBR® Green PCR Master Mix (ABI) with 102 µl cDNA sample and 1173 µl nuclease-free water to create of premix of all the PCR components for a single sample except for the PCR primers. After mixing, 25 aliquots were dispensed into each well of the PCR array and all wells capped or sealed. PCR arrays are PCR instrument specific plastic plates into which the primers for a specific PCR assay have been pre-dispensed and dried into reaction wells at indexed positions on the plate. One 96-well PCR plate is therefore an array of 84 experimental gene assays of interest with 12 reaction wells of the control assay panel described in this invention. Real-time PCR thermal cycling and detection was performed on either an ABI 7500 (Applied Biosystems, Foster City, Calif.) or Stratagene Mx3005P (La Jolla, Calif.) instrument programmed for thermal cycling conditions of 10 minutes at 95° C., then 40 cycles of 15 seconds each at 95° C., followed by 60 seconds at 60° C.

Using the instrument's software and a consistent selection of measurement variables, $C_t$ values were determined. The positive plate control or PPC assay is first used at this stage to guide the user in establishing an appropriate cycle threshold value for array plates on this instrument. When the threshold value intersects the middle of the logarithmic portion of the PPC amplification curve it should return a $C_t$ value of approximately 20. This exact value may vary from instrument to instrument but once established for a single instrument and a fixed threshold setting PPC assays should return very consistent values on every array plate if the PCR was successful. Failure of the PPC assay to produce a sigmoidal shaped amplification curve or a sigmoidal curve that starts to rise above background later than 30 cycles or a large variation in the $C_t$ values from this assay, as indicated by a standard deviation of the $C_t > 0.5$, across the experimental plates all indicate a failure of at least one critical PCR component in that run. The data from that plate cannot be considered quantitative and should not be used for experimental analysis where a quantitative result is needed.

Once an appropriate threshold value has been established, the efficiency of reverse transcription can be assessed to confirm equivalence across all samples being evaluated. The first step utilizes an intra-plate comparison by comparing the $C_t$ for the spiked in RTC RNA template to the $C_t$ from the PPC assay. The $C_t$ values for both of these assays are based on predefined amounts of template that were exogenously added to the reactions and therefore expected to give a consistent $C_t$ value relative to each other when the RT and PCR reactions proceed with high efficiency. As prepared, the amount of RTC template in a PCR well is 5 fold less than that for the PPC. When the PPC $C_t$ is subtracted from the RTC $C_t$ and that value is less than 5.0, the RT reaction is deemed to have acceptable amplification efficiency. The second step examines the standard deviation of the $C_t$ values for the RTC assay from all array plates in the experiment. An acceptable level of variation has a standard deviation of less than 0.5.

To determine whether there is generally an unacceptably high level of genomic DNA contamination carrying over into the cDNA sample from the original RNA isolation, the GDC assay is analyzed. If there is a significant level of genomic DNA contamination, then accuracy of the other assays on the plate is compromised, and the $C_t$ value for the assay will be less than 35.

Once the control panel results have been assessed and determined to meet consistent quality criteria, then accurate relative gene expression measurements can be obtained by the ΔΔCt calculation method (Livak, K J and Schmittgen, T D. 2001 Methods. December 25(4):402-8) using all or a subset of HKG assays from the control panel.

What is claimed is:

1. A multi-well PCR array, comprising:
   (a) in a first well, a primer pair designed for amplifying a Genomic DNA Contamination Control (GDC) sequence, wherein
   when the GDC sequence is a human genomic DNA sequence, one primer of the primer pair comprises SEQ ID NO:7 and the other primer of the primer pair comprises SEQ ID NO:8, or one primer of the primer pair comprises SEQ ID NO:9 and the other primer of the primer pair comprises SEQ ID NO:10;
   when the GDC sequence is a mouse genomic DNA sequence, one primer of the primer pair comprises SEQ ID NO:13 and the other primer of the primer pair comprises SEQ ID NO:14; or
   when the GDC sequence is rat genomic DNA sequence, one primer of the primer pair comprises SEQ ID NO:15 and the other primer comprises SEQ ID NO:16; and
   (b) in a second well, a Plate Positive Control (PPC) template nucleic acid and a primer pair designed for amplifying the PPC template, wherein one primer of the primer pair designed for amplifying the PPC template nucleic acid comprises SEQ ID NO: 4 and the other primer of the primer pair designed for amplifying the PPC template nucleic acid comprises SEQ ID NO:5.

2. The multi-well PCR array of claim 1, wherein the PPC template nucleic acid comprises SEQ ID NO:6.

3. The multi-well PCR array of claim 1, further comprising:
   (c) in a third well, a primer pair designed for amplifying the cDNA of a Reverse Transcription Control (RTC) RNA.

4. The multi-well PCR array of claim 3, wherein one primer of the primer pair designed for amplifying the cDNA of the RTC RNA comprises SEQ ID NO:1 and the other primer of the primer pair designed for amplifying the cDNA of the RTC RNA comprises SEQ ID NO:2.

5. The multi-well PCR array of claim 3, further comprising:
   (d) in the fourth well, a primer pair designed for amplifying a house keeping gene (HKG).

6. The multi-well PCR array of claim 5, wherein when the GDC sequence is a human genomic DNA sequence, the HKG is selected from the group consisting of human beta-2-microglobulin (B2M), hypoxanthine guanine phosphoribosyl transferase 1 (HPRT1), ribosomal protein L 13a (RPL 13A), glyceraldehydes-3-phosphate dehydrogenase (GAPDH), and actin, beta (ACTB) genes.

7. The multi-well PCR array of claim 5, wherein when the GDC sequence is a human genomic DNA sequence, the primer pair designed for amplifying the HKG comprises SEQ ID NO:17 and SEQ ID NO:18, SEQ ID NO:19 and SEQ ID NO:20, SEQ ID NO:21 and SEQ ID NO:22, SEQ ID NO:23 and SEQ ID NO:24, or SEQ ID NO:25 and SEQ ID NO:26.

8. The multi-well PCR array of claim 5, wherein when the GDC sequence is a mouse genomic DNA sequence, the HKG is selected from the group consisting of mouse glucuronidase, beta (Gusb), hypoxanthine guanine phosphoribosyl transferase 1 (HPRT1), heat shock protein 90 kpa alpha class B member 1 (Hsp90ab1), glyceraldehydes-3-phosphate dehydrogenase (GAPDH), and actin, beta (ACTB) genes.

9. The multi-well PCR array of claim 5, wherein when the GDC sequence is a mouse genomic DNA sequence, the primer pair designed for amplifying the HKG comprises SEQ ID NO:27 and SEQ ID NO:28, SEQ ID NO:29 and SEQ ID NO:30, SEQ ID NO:31 and SEQ ID NO:32, SEQ ID NO:33 and SEQ ID NO:34, or SEQ ID NO:35 and SEQ ID NO:36.

10. The multi-well PCR array of claim 5, wherein when the GDC sequence is a rat genomic DNA sequence, the HKG is selected from the group consisting of rat ribosomal protein, large P1 (Rplp1), hypoxanthine guanine phosphoribosyl transferase (HPRT), ribosomal protein L 13a (Rpl13A), lactate dehydrogenase A (Ldha), and actin, beta (Actb) genes.

11. The multi-well PCR array of claim 5, wherein when the GDC sequence is a rat genomic DNA sequence, the primer pair designed for amplifying the HKG comprises SEQ ID NO:37 and SEQ ID NO:38, SEQ ID NO:39 and SEQ ID NO:40, SEQ ID NO:41 and SEQ ID NO:42, SEQ ID NO:43 and SEQ ID NO:44, or SEQ ID NO:45 and SEQ ID NO:46.

* * * * *

UNITED STATES PATENT AND TRADEMARK OFFICE
CERTIFICATE OF CORRECTION

| | | |
|---|---|---|
| PATENT NO. | : 8,597,938 B2 | Page 1 of 1 |
| APPLICATION NO. | : 12/249791 | |
| DATED | : December 3, 2013 | |
| INVENTOR(S) | : Jingping Yang et al. | |

It is certified that error appears in the above-identified patent and that said Letters Patent is hereby corrected as shown below:

In the Claims

Column 28, Line 40:
"transferase 1 (HPRT1), heat shock protein 90 kpa alpha class B" should read, --transferase 1 (HPRT1), heat shock protein 90kDa alpha class B--.

Signed and Sealed this
Sixteenth Day of September, 2014

Michelle K. Lee
*Deputy Director of the United States Patent and Trademark Office*

SEQUENCE LISTING

<160> NUMBER OF SEQ ID NOS: 46

<210> SEQ ID NO 1
<211> LENGTH: 20
<212> TYPE: DNA
<213> ORGANISM: Artificial Sequence
<220> FEATURE:
<223> OTHER INFORMATION: Synthetic construct: oligonucleotide useful
      as a primer.

<400> SEQUENCE: 1
gggtggaggt ccctatggtc                                              20

<210> SEQ ID NO 2
<211> LENGTH: 20
<212> TYPE: DNA
<213> ORGANISM: Artificial Sequence
<220> FEATURE:
<223> OTHER INFORMATION: Synthetic construct: sequence as primer.

<400> SEQUENCE: 2
ctgcaccacg gagatcagct                                              20

<210> SEQ ID NO 3
<211> LENGTH: 593
<212> TYPE: DNA
<213> ORGANISM: Artificial Sequence
<220> FEATURE:
<223> OTHER INFORMATION: Synthetic construct: polynucleotide useful
      as RTC control.

<400> SEQUENCE: 3
ctcgttgttc tcctgctgca acatctctca gaaaccatct ctcttttctc cgtcttctcg        60
tagttctcat tgtcccattc gttgctcaca gtcacaggaa gggaagaag tggttaccag        120 tcctttgaga agtgtggttt ggtcattagg agaagaggtt tcaaagagaa gtctatttgc        180
acttgtctct gcttctctct tctttgttga tcctgctctt gcttttaagg gtggaggtcc        240
ctatggtcaa ggagtcacca ggggacagga cctatctggc aaagatttca gtggccagac        300
tcttatcagg caggacttca aaacgtccat cctaaggcaa gccaacttca agggtgcaaa        360
gttgttaggt gctagcttct ttgatgcaga tctaacaggt gctgatttat cggaagctga        420
tctccgaggt gcagatttct ccttggcaaa tgtaacaaag gtgaatctaa cgaacgctaa       480

```
cttagaagga gcgactgtta ctggaaacac atcattcaag ggatcaaaca ttgcaggcgc      540
agacttcact gatgtcccgg gcgagctccc aaaaaaaaaa aaaaaccgaa ttc             593

<210> SEQ ID NO 4
<211> LENGTH: 18
<212> TYPE: DNA
<213> ORGANISM: Artificial Sequence
<220> FEATURE:
<223> OTHER INFORMATION: Synthetic construct:  oligonucleotide useful
      as a primer.

<400> SEQUENCE: 4
agctgatctc cgaggtgc                                                    18

<210> SEQ ID NO 5
<211> LENGTH: 21
<212> TYPE: DNA
<213> ORGANISM: Artificial Sequence
<220> FEATURE:
<223> OTHER INFORMATION: Synthetic construct:  Oligonucleotide useful
      as a primer.

<400> SEQUENCE: 5
ctctcgtacc gtgtttgctg t                                                21

<210> SEQ ID NO 6
<211> LENGTH: 637
<212> TYPE: DNA
<213> ORGANISM: Artificial Sequence
<220> FEATURE:
<223> OTHER INFORMATION: Synthetic construct:  polynucleotide useful
      as a PPC control.

<400> SEQUENCE: 6
cctgctgcaa catctctcag aaaccatctc tcttttctcc gtcttctcgt agttctcatt      60
gtcccattcg ttgctcacag tcacaggaag ggaaagaagt ggttaccagt cctttgagaa     120
gtgtggtttg gtcattagga gaagaggttt caaagagaag tctatttgca cttgtctctg     180
cttctctctt ctttgttgat cctgctcttg cttttaaggg tggaggtccc tatggtcaag     240
gagtcaccag gggacaggac ctatctggca aagatttcag tggccagact cttatcaggc     300
aggacttcaa aacgtccatc ctaaggcaag ccaacttcaa gggtgcaaag ttgttaggtg     360
ctagcttctt tgatgcagat ctaacaggtg ctgatttatc ggaagctgat ctccgaggtg     420
cagatttctc cttggcaaat gtaacaaagg tgaatctaac gaacgctaac ttagaaggag     480
cgactgttac tggaaacaca tcattcaagg atcaaacat tgcaggcgca gacttcactg     540 atgtccctg gtcgatggta cggatggttg tatagatata cacaatcaac agcaaacacg     600
gtacgagagc tcccaaaaaa aaaaaaaaac cgaattc                             637

<210> SEQ ID NO 7
<211> LENGTH: 20
<212> TYPE: DNA
<213> ORGANISM: Artificial Sequence
<220> FEATURE:
<223> OTHER INFORMATION: Synthetic construct:  oligonucleotide useful
      as control in reactions with human samples.

<400> SEQUENCE: 7
gattgcattc aagtcacaca                                                  20

<210> SEQ ID NO 8
<211> LENGTH: 19
<212> TYPE: DNA
```

```
<213> ORGANISM: Artificial Sequence
<220> FEATURE:
<223> OTHER INFORMATION: Synthetic construct: oligonucleotide useful
      as a control primer in reactions with human samples.

<400> SEQUENCE: 8
gctcgaacac aaacatcac                                                   19

<210> SEQ ID NO 9
<211> LENGTH: 20
<212> TYPE: DNA
<213> ORGANISM: Artificial Sequence
<220> FEATURE:
<223> OTHER INFORMATION: Synthetic construct: oligonucleotide useful
      as a control primer in reactions with human samples

<400> SEQUENCE: 9
cacccatgat atgccttagc                                                  20

<210> SEQ ID NO 10
<211> LENGTH: 19
<212> TYPE: DNA
<213> ORGANISM: Artificial Sequence
<220> FEATURE:
<223> OTHER INFORMATION: Synthetic construct: oligonucleotide useful
      as a control primer in reactions with human samples.

<400> SEQUENCE: 10
ttctgctgaa cccaagagc                                                   19

<210> SEQ ID NO 11
<211> LENGTH: 20
<212> TYPE: DNA
<213> ORGANISM: Artificial Sequence
<220> FEATURE:
<223> OTHER INFORMATION: Synthetic construct: oligonucleotide useful
      as a control primer in reactions with mouse samples.

<400> SEQUENCE: 11
ttaggacgtg aagtttggtg                                                  20

<210> SEQ ID NO 12
<211> LENGTH: 19
<212> TYPE: DNA
<213> ORGANISM: Artificial Sequence
<220> FEATURE:
<223> OTHER INFORMATION: Synthetic construct: oligonucleotide useful
      as a control primer in reactions with mouse samples.

<400> SEQUENCE: 12
ccttcagtgt gcatttctc                                                   19

<210> SEQ ID NO 13
<211> LENGTH: 19
<212> TYPE: DNA
<213> ORGANISM: Artificial Sequence
<220> FEATURE:
<223> OTHER INFORMATION: Synthetic construct: oligonucleotide useful
      as a control primer in reactions with mouse samples.

<400> SEQUENCE: 13
atcccatgat gttgccaag                                                   19

<210> SEQ ID NO 14
<211> LENGTH: 19
<212> TYPE: DNA
<213> ORGANISM: Artificial Sequence
<220> FEATURE:
```

```
<223> OTHER INFORMATION: Synthetic construct: oligonucleotide useful
      as a control primer in reactions with mouse samples.

<400> SEQUENCE: 14
tgtctggctc ggtgtttac                                                    19

<210> SEQ ID NO 15
<211> LENGTH: 22
<212> TYPE: DNA
<213> ORGANISM: Artificial Sequence
<220> FEATURE:
<223> OTHER INFORMATION: Synthetic construct: oligonucleotide useful
      as a control primer in reactions with rat samples.

<400> SEQUENCE: 15
tctgcctctc aataccatca tc                                                22

<210> SEQ ID NO 16
<211> LENGTH: 22
<212> TYPE: DNA
<213> ORGANISM: Artificial Sequence
<220> FEATURE:
<223> OTHER INFORMATION: Synthetic construct: oligonucleotide useful
      as a control primer in reactions with rat samples.

<400> SEQUENCE: 16
tgaacaaaga gaaactgtcc ag                                                22

<210> SEQ ID NO 17
<211> LENGTH: 23
<212> TYPE: DNA
<213> ORGANISM: Artificial Sequence
<220> FEATURE:
<223> OTHER INFORMATION: Synthetic construct: olignucleotide useful
      as control human beta-2-microglobulin primer.

<400> SEQUENCE: 17
gcaaggactg gtctttctat ctc                                               23

<210> SEQ ID NO 18
<211> LENGTH: 23
<212> TYPE: DNA
<213> ORGANISM: Artificial Sequence
<220> FEATURE:
<223> OTHER INFORMATION: Synthetic construct: olignucleotide useful
      as control human beta-2-microglobulin primer.

<400> SEQUENCE: 18
acttaactat cttgggctgt gac                                               23

<210> SEQ ID NO 19
<211> LENGTH: 20
<212> TYPE: DNA
<213> ORGANISM: Artificial Sequence
<220> FEATURE:
<223> OTHER INFORMATION: Synthetic construct: oligonucleotide useful
      as a human HPRT1 primer.

<400> SEQUENCE: 19
ggccatctgc ttagtagagc                                                   20

<210> SEQ ID NO 20
<211> LENGTH: 20
<212> TYPE: DNA
<213> ORGANISM: Artificial Sequence
<220> FEATURE:
<223> OTHER INFORMATION: Synthetic construct: oligonucleotide useful
      as a human HPRT1 primer.
```

<210> SEQ ID NO 20
<211> LENGTH: 20
<212> TYPE: DNA
<213> ORGANISM: Artificial Sequence
<220> FEATURE:
<223> OTHER INFORMATION: Synthetic construct: oligonucleotide useful
    as a human RPL 13A primer.

<400> SEQUENCE: 20
ttaggaatgc agcaactgac                                              20

<210> SEQ ID NO 21
<211> LENGTH: 21
<212> TYPE: DNA
<213> ORGANISM: Artificial Sequence
<220> FEATURE:
<223> OTHER INFORMATION: Synthetic construct: oligonucleotide useful
    as a human RPL 13A primer.

<400> SEQUENCE: 21
tgagtgaaag ggagccagaa g                                            21

<210> SEQ ID NO 22
<211> LENGTH: 21
<212> TYPE: DNA
<213> ORGANISM: Artificial Sequence
<220> FEATURE:
<223> OTHER INFORMATION: Synthetic construct: oligonucleotide useful
    as a human RPL 13A primer.

<400> SEQUENCE: 22
tgcagagtat atgaccaggt g                                            21

<210> SEQ ID NO 23
<211> LENGTH: 22
<212> TYPE: DNA
<213> ORGANISM: Artificial Sequence
<220> FEATURE:
<223> OTHER INFORMATION: Synthetic construct: oligonucleotide useful
    as a human GAPDH primer.

<400> SEQUENCE: 23
agagcacaag aggaagagag ag                                           22

<210> SEQ ID NO 24
<211> LENGTH: 24
<212> TYPE: DNA
<213> ORGANISM: Artificial Sequence
<220> FEATURE:
<223> OTHER INFORMATION: Synthetic construct: oligonucleotide useful
    as a human GAPDF primer.

<400> SEQUENCE: 24
ggttgagcac agggtacttt attg                                         24

<210> SEQ ID NO 25
<211> LENGTH: 21
<212> TYPE: DNA
<213> ORGANISM: Artificial Sequence
<220> FEATURE:
<223> OTHER INFORMATION: Synthetic construct oligonucleotide useful
    as a human ACTB primer.

<400> SEQUENCE: 25
aatgcttcta ggcggactat g                                            21

<210> SEQ ID NO 26
<211> LENGTH: 20
<212> TYPE: DNA
<213> ORGANISM: Artificial Sequence
<220> FEATURE:
<223> OTHER INFORMATION: Synthetic construct oligonucleotide useful
    as a human ACTB primer.

<400> SEQUENCE: 26
ctccaaccga ctgctgtcac                                                20

<210> SEQ ID NO 27
<211> LENGTH: 23
<212> TYPE: DNA
<213> ORGANISM: Artificial Sequence
<220> FEATURE:
<223> OTHER INFORMATION: Synthetic construct: oligonucleotide useful
      as a mouse Gusb primer.

<400> SEQUENCE: 27
gtaatatgtc ctgctgagag gtg                                            23

<210> SEQ ID NO 28
<211> LENGTH: 22
<212> TYPE: DNA
<213> ORGANISM: Artificial Sequence
<220> FEATURE:
<223> OTHER INFORMATION: Synthetic construct: oligonucleotide useful
      as a mouse Gusb primer.

<400> SEQUENCE: 28
cttaaattgt gagccagcct tc                                             22

<210> SEQ ID NO 29
<211> LENGTH: 20
<212> TYPE: DNA
<213> ORGANISM: Artificial Sequence
<220> FEATURE:
<223> OTHER INFORMATION: Synthetic construct: oligonucleotide useful
      as a mouse Hprt1 primer.

<400> SEQUENCE: 29
ggccatctgc ctagtaaagc                                                20

<210> SEQ ID NO 30
<211> LENGTH: 21
<212> TYPE: DNA
<213> ORGANISM: Artificial Sequence
<220> FEATURE:
<223> OTHER INFORMATION: Synthetic construct: oligonucleotide useful
      as a mouse Hprt1 primer.

<400> SEQUENCE: 30
ggacgcagca actgacattt c                                              21

<210> SEQ ID NO 31
<211> LENGTH: 23
<212> TYPE: DNA
<213> ORGANISM: Artificial Sequence
<220> FEATURE:
<223> OTHER INFORMATION: Synthetic construct: oligonucleotide useful
      as a mouse Hsp90ab1 primer.

<400> SEQUENCE: 31
ggctctctgc tcatgtctac aag                                            23

<210> SEQ ID NO 32
<211> LENGTH: 23
<212> TYPE: DNA
<213> ORGANISM: Artificial Sequence
<220> FEATURE:
<223> OTHER INFORMATION: Synthetic construct: oligonucleotide useful
      as a mouse Hsp90ab1 primer.

<400> SEQUENCE: 32
aaccacaata cataacaccc aac                                            23

```
<210> SEQ ID NO 33
<211> LENGTH: 24
<212> TYPE: DNA
<213> ORGANISM: Artificial Sequence
<220> FEATURE:
<223> OTHER INFORMATION: Synthetic construct:  oligonucleotide useful
      as a mouse Gapdh primer.

<400> SEQUENCE: 33
tatgactcca ctcacggcaa attc                                              24

<210> SEQ ID NO 34
<211> LENGTH: 20
<212> TYPE: DNA
<213> ORGANISM: Artificial Sequence
<220> FEATURE:
<223> OTHER INFORMATION: Synthetic construct:  oligonucleotide useful
      as a mouse Gapdh primer.

<400> SEQUENCE: 34
acatactcag caccggcctc                                                   20

<210> SEQ ID NO 35
<211> LENGTH: 20
<212> TYPE: DNA
<213> ORGANISM: Artificial Sequence
<220> FEATURE:
<223> OTHER INFORMATION: Synthetic construct:  oligonucleotide useful
      as a mouse Actb primer.

<400> SEQUENCE: 35
ggctgtattc ccctccatcg                                                   20

<210> SEQ ID NO 36
<211> LENGTH: 22
<212> TYPE: DNA
<213> ORGANISM: Artificial Sequence
<220> FEATURE:
<223> OTHER INFORMATION: Synthetic construct:  oligonucleotide useful
      as a mouse Actb primer.

<400> SEQUENCE: 36
ccagttggta acaatgccat gt                                                22

<210> SEQ ID NO 37
<211> LENGTH: 19
<212> TYPE: DNA
<213> ORGANISM: Artificial Sequence
<220> FEATURE:
<223> OTHER INFORMATION: Synthetic construct:  oligonucleotide useful
      as a rat  Rplp1 primer.

<400> SEQUENCE: 37
ctaaggccgc gttgaggtg                                                    19

<210> SEQ ID NO 38
<211> LENGTH: 22
<212> TYPE: DNA
<213> ORGANISM: Artificial Sequence
<220> FEATURE:
<223> OTHER INFORMATION: Synthetic construct:  oligonucleotide useful
      as a rat Rplp1 primer.

<400> SEQUENCE: 38
caggcaagct cagagacaga ag                                                22
```

-continued

```
<210> SEQ ID NO 39
<211> LENGTH: 23
<212> TYPE: DNA
<213> ORGANISM: Artificial Sequence
<220> FEATURE:
<223> OTHER INFORMATION: Synthetic construct:  oligonucleotide useful
      as a rat Hprt primer.

<400> SEQUENCE: 39
ttagaaatgt ctgttgctgc gtc                                              23

<210> SEQ ID NO 40
<211> LENGTH: 24
<212> TYPE: DNA
<213> ORGANISM: Artificial Sequence
<220> FEATURE:
<223> OTHER INFORMATION: Synthetic construct:  oligonucleotide useful
      as a rat Hprt primer.

<400> SEQUENCE: 40
gatctgtctg tctcacaagg gaag                                             24

<210> SEQ ID NO 41
<211> LENGTH: 21
<212> TYPE: DNA
<213> ORGANISM: Artificial Sequence
<220> FEATURE:
<223> OTHER INFORMATION: Synthetic construct:  oligonucleotide useful
      as a rat Rpl13A primer.

<400> SEQUENCE: 41
agtatctggc ctttctccga a                                                21

<210> SEQ ID NO 42
<211> LENGTH: 21
<212> TYPE: DNA
<213> ORGANISM: Artificial Sequence
<220> FEATURE:
<223> OTHER INFORMATION: Synthetic construct:  oligonucleotide useful
      as a rat Rpl13A primer.

<400> SEQUENCE: 42
gatcccatcc aacaccttga g                                                21

<210> SEQ ID NO 43
<211> LENGTH: 22
<212> TYPE: DNA
<213> ORGANISM: Artificial Sequence
<220> FEATURE:
<223> OTHER INFORMATION: Synthetic construct:  oligonucleotide useful
      as a rat Ldha primer.

<400> SEQUENCE: 43
agctgaaagg ttacacatcc tg                                               22

<210> SEQ ID NO 44
<211> LENGTH: 21
<212> TYPE: DNA
<213> ORGANISM: Artificial Sequence
<220> FEATURE:
<223> OTHER INFORMATION: Synthetic construct:  oligonucleotide useful
      as a rat Ldha primer.

<400> SEQUENCE: 44
ttcattatgc tctcggccaa g                                                21

<210> SEQ ID NO 45
<211> LENGTH: 22
```

```
<212> TYPE: DNA
<213> ORGANISM: Artificial Sequence
<220> FEATURE:
<223> OTHER INFORMATION: Synthetic construct: oligonucleotide useful
      as a rat Actb primer.

<400> SEQUENCE: 45
tgtgtggatt ggtggctcta tc                                          22

<210> SEQ ID NO 46
<211> LENGTH: 23
<212> TYPE: DNA
<213> ORGANISM: Artificial Sequence
<220> FEATURE:
<223> OTHER INFORMATION: Synthetic construct: oligonucleotide useful
      as a rat Actb primer.

<400> SEQUENCE: 46
ctcagtaaca gtccgcctag aag                                         23
```